United States Patent
Fukuda

(10) Patent No.: US 10,966,649 B2
(45) Date of Patent: Apr. 6, 2021

(54) BIOELECTRODE SHEET

(71) Applicant: Fukuda Denshi Co., Ltd., Tokyo (JP)

(72) Inventor: Yutaka Fukuda, Tokyo (JP)

(73) Assignee: FUKUDA DENSHI CO., LTD., Tokyo (JP)

( * ) Notice: Subject to any disclaimer, the term of this patent is extended or adjusted under 35 U.S.C. 154(b) by 0 days.

(21) Appl. No.: 16/494,323

(22) PCT Filed: Mar. 14, 2018

(86) PCT No.: PCT/JP2018/009969
§ 371 (c)(1),
(2) Date: Sep. 16, 2019

(87) PCT Pub. No.: WO2018/168925
PCT Pub. Date: Sep. 20, 2018

(65) Prior Publication Data
US 2020/0009072 A1   Jan. 9, 2020

(30) Foreign Application Priority Data
Mar. 16, 2017   (JP) .............................. JP2017-051690

(51) Int. Cl.
*A61B 5/0408*   (2006.01)
*A61B 5/25*   (2021.01)
(Continued)

(52) U.S. Cl.
CPC ................ *A61B 5/25* (2021.01); *A61B 5/259* (2021.01); *A61B 5/274* (2021.01); *A61B 5/282* (2021.01);
(Continued)

(58) Field of Classification Search
CPC .............. A61B 5/0408; A61B 5/04082; A61B 5/04085; A61B 5/04087; A61B 5/0416; A61B 2562/0209
See application file for complete search history.

(56) References Cited

U.S. PATENT DOCUMENTS

| 4,114,263 A | * | 9/1978 | Szpur | ................... | A61B 5/0408 29/877 |
|---|---|---|---|---|---|
| 4,166,453 A | * | 9/1979 | McClelland | ......... | A61B 5/0408 600/396 |

(Continued)

FOREIGN PATENT DOCUMENTS

| JP | 06-245915 A | 9/1994 |
|---|---|---|
| JP | 11-349786 A | 12/1999 |

(Continued)

OTHER PUBLICATIONS

International Search Report from International Application No. PCT/JP2018/009969 dated May 22, 2018.

*Primary Examiner* — Eun Hwa Kim
(74) *Attorney, Agent, or Firm* — Brundidge & Stanger, P.C.

(57) ABSTRACT

A bioelectrode sheet (100) is configured to be affixed to the skin of a subject, a drug (104*b*) being mixed in an adhesive layer (104) provided at a peripheral position of a conductive gel layer (103) so as to avoid the conductive gel layer (103). The drug (104*b*) admixed with the adhesive layer (104) can thereby be caused to penetrate the body while biological information is acquired by an electrode (102) via the conductive gel layer (103).

5 Claims, 4 Drawing Sheets

(51) Int. Cl.
    *A61K 9/70*   (2006.01)
    *A61M 35/00*  (2006.01)
    *A61B 5/259*  (2021.01)
    *A61B 5/274*  (2021.01)
    *A61B 5/282*  (2021.01)

(52) U.S. Cl.
    CPC .......... *A61K 9/7038* (2013.01); *A61M 35/10* (2019.05); *A61B 2562/0209* (2013.01)

(56) References Cited

U.S. PATENT DOCUMENTS

| | | | | |
|---|---|---|---|---|
| 4,350,165 | A | * 9/1982 | Striese | A61B 5/0408 |
| | | | | 600/397 |
| 5,483,967 | A | 1/1996 | Ohtake | |
| 5,823,957 | A | * 10/1998 | Faupel | A61B 5/04087 |
| | | | | 600/397 |
| 6,121,508 | A | * 9/2000 | Bischof | A61B 5/04087 |
| | | | | 428/355 AC |
| 2012/0058175 | A1 | 3/2012 | Amano | |
| 2013/0324828 | A1 | 12/2013 | Nishiwaki | |
| 2013/0325096 | A1 | 12/2013 | Dupelle | |
| 2017/0164841 | A1* | 6/2017 | Katra | A61B 5/0002 |

FOREIGN PATENT DOCUMENTS

| | | |
|---|---|---|
| JP | 2001-269322 A | 10/2001 |
| JP | 3429198 B2 | 5/2003 |
| JP | 2006-290858 A | 10/2006 |
| JP | 2013-252180 A | 12/2013 |
| JP | 2015-521085 A | 7/2015 |
| KR | 20120023658 A | 3/2012 |
| KR | 20120139347 A | 12/2012 |

\* cited by examiner

BIOELECTRODE SHEET

TECHNICAL FIELD

The present invention relates to a bioelectrode sheet for measuring, for example, an electrocardiogram.

BACKGROUND ART

A surface electrocardiogram is obtained by affixing a bioelectrode sheet including an electrode fitted therein to a body surface of a subject and measuring an electric potential received through this bioelectrode sheet by an electrocardiograph. The bioelectrode sheet of this type is described, for example, in Patent Literature (hereinafter, abbreviated as PTL) 1 and PTL 2.

PTL 3 also describes a bioelectrode sheet including conductive gel. The conductive gel disposed between a probe and a skin can help to improve conductivity between the probe and the skin. In consideration of the bioelectrode sheet affixed to the skin for the long period of time, PTL 3 further describes that such a material of the conductive gel is used that dermal inflammation hardly occurs even in a case where the bioelectrode sheet is affixed for a period of at least approximately one week.

CITATION LIST

Patent Literature

PTL 1
Japanese Patent Application Laid-Open No. H6-245915
PTL 2
Japanese Patent Application Laid-Open No. 2001-269322
PTL 3
Japanese Unexamined Patent Application Publication (Translation of PCT Application) No. 2015-521085
PTL 4
Japanese Patent No. 3429198

SUMMARY OF INVENTION

Technical Problem

The inventors of the present invention have considered to take advantage of characteristics of the bioelectrode sheet such as being affixed to the body surface for the long period of time as described above, and completed the present invention.

An object of the present invention is to provide a bioelectrode sheet usable for other purposes in addition to measurement for biological information without decreasing measurement accuracy for biological information such as an electrocardiogram.

Solution to Problem

One aspect of a bioelectrode sheet of the present invention is a bioelectrode sheet to be affixed to a skin of a subject, the bioelectrode sheet including:

a sheet-like base including first and second surfaces;

an electrode held by the base, at least a part of the electrode being disposed on a side of the first surface of the base;

a conductive gel layer that covers the at least part of the electrode disposed on the side of the first surface of the base and is exposed to the side of the first surface; and an adhesive layer that is disposed in a position different from the conductive gel layer of the base and is exposed to the side of the first surface in a position different from the conductive gel layer, in which the adhesive layer includes medicament mixed in the adhesive layer.

Advantageous Effects of Invention

In accordance with the present invention, since the medicament mixed in the adhesive layer may be caused to permeate the body from the skin while the biological information is obtained by the electrode via the conductive gel layer, it is possible to realize the bioelectrode sheet to be also usable for other purpose than the measurement for the biological information without decreasing the measurement accuracy for the biological information such as the electrocardiogram.

DESCRIPTION OF EMBODIMENTS

Hereinafter, an embodiment of the present invention will be described in detail with reference to the accompanied drawings.

Figure 1:
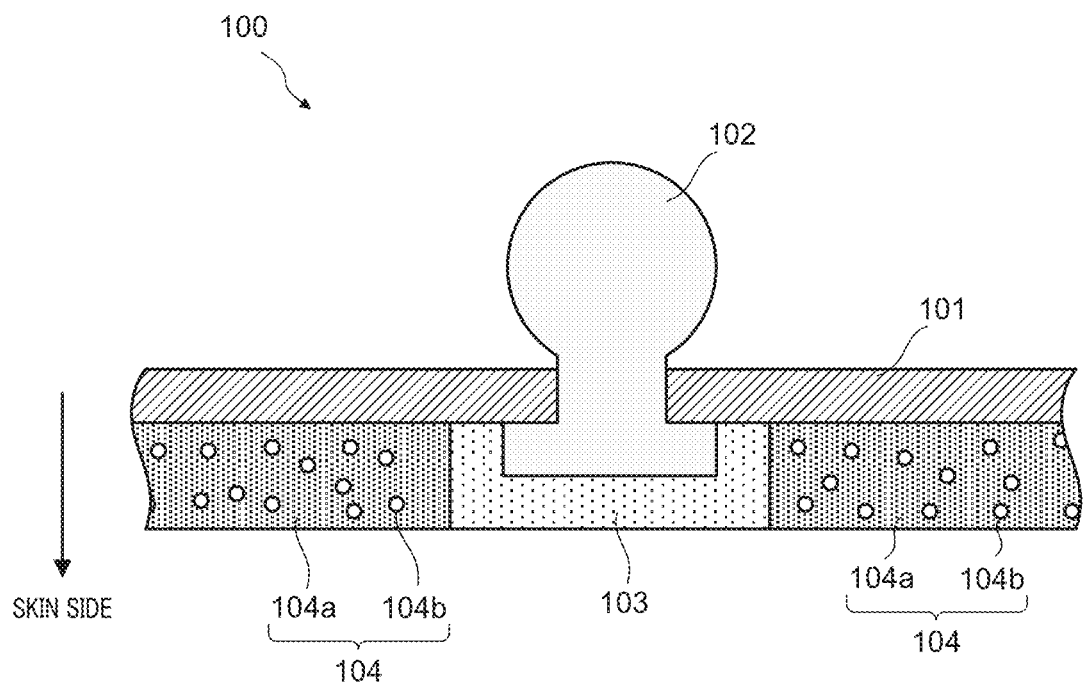
FIG. 1 is a cross sectional diagram illustrating a main part configuration of a bioelectrode sheet according to an embodiment.

FIG. 1 is a cross sectional diagram illustrating a main part configuration of a bioelectrode sheet according to the embodiment of the present invention. Bioelectrode sheet 100 is affixed to a skin (body surface) of a subject. Bioelectrode sheet 100 according to the present embodiment is to be affixed to a chest or other position of the subject and is used to measure an electrocardiogram of the subject.

In bioelectrode sheet 100, electrode 102 is attached to sheet-like base 101. Base 101 is made of a nonconductive material having flexibility such as, for example, polyurethane. Electrode 102 is made, for example, of Ag/AgCl (silver/silver chloride) or the like. Electrode 102 is attached to base 101 so as to penetrate through base 101, and at least a part of the electrode is disposed on a first surface side of base 101. Herein, a first surface of base 101 is a surface on a skin side of base 101 when bioelectrode sheet 100 is affixed to the skin. A lead line or the like to be led to an electrocardiogram measuring apparatus or a recording apparatus is connected to a part of electrode 102 that is exposed to a second surface side that is an opposite side of the first surface of base 101. A shape of electrode 102 is not limited to the shape illustrated in FIG. 1, of course.

Conductive gel layer 103 is formed on the first surface side of base 101. Conductive gel layer 103 is formed to cover electrode 102 disposed on the first surface side of base 101 to be exposed to the first surface side. A material such as electrolyte gel that may increase conductivity between the skin and electrode 102 is used as conductive gel layer 103.

Adhesive layer 104 is also formed on the first surface side of base 101. Adhesive layer 104 is formed in a peripheral position of conductive gel layer 103 without interference with conductive gel layer 103. In practice, conductive gel layer 103 is circular as observed from the skin side, and adhesive layer 104 is formed so as to be adjacent to conductive gel layer 103 in a position where no interference is caused with circular conductive gel layer 103.

Adhesive layer 104 is formed by mixing medicament 104b in adhesive agent 104a. Adhesive agent that hardly causes inflammation or itching on the skin as being used in a general medical adhesive tape is used as adhesive agent 104a.

Medicament 104b is medicament of a percutaneous absorption type. According to the present embodiment, medicament such as Bisoprolol working for a cardiovascular system is used as medicament 104b. Bisoprolol is medicament effective to hypertension. Of course, other medicament of the percutaneous absorption type may be used as medicament 104b, or inactive ingredients or the like may be further mixed.

Herein, electrical resistance of adhesive layer 104 is set to be significantly higher than electrical resistance of conductive gel layer 103. Thus, a bioelectric potential (biological information) measured via electrode 102 is hardly affected by influences of adhesive layer 104. As a result, since the electric potential to be measured by electrode 102 is hardly affected by the type and concentration of medicament 104b, the degree of freedom for the choice of medicament 104b is increased as compared with a case where the medicament is mixed in conductive gel layer 103, for example. In addition, since medicament 104b hardly receives electric influences, the adverse influences by the current into medicament 104b may be ignored as compared with a case where the medicament is mixed in conductive gel layer 103.

Figure 2:
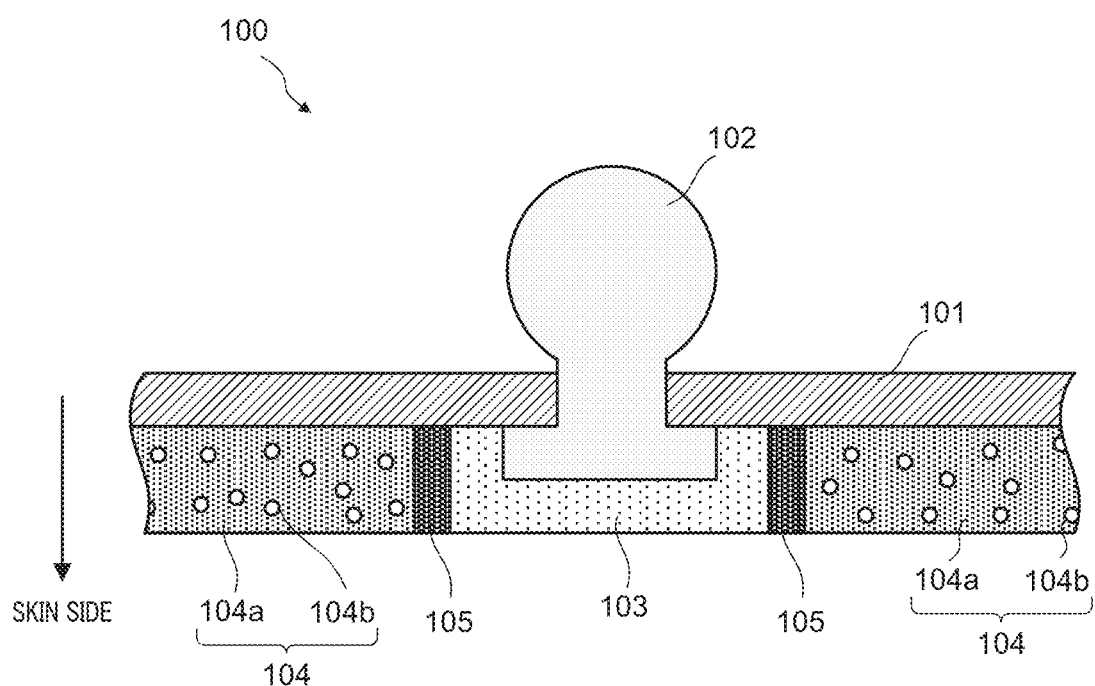
FIG. 2 is a cross sectional diagram illustrating another configuration example of the bioelectrode sheet.

As illustrated in FIG. 2, adhesive layer (also referred to as stopper) 105 may be disposed between conductive gel layer 103 and adhesive layer 104. Adhesive layer 105 is an adhesive layer where the medicament is not mixed. Adhesive layer 105 has higher adhesive force than adhesive layer 104. Adhesive layer 105 is preferably an insulating layer. With the above-described configuration, the flow of medicament 104b into conductive gel layer 103 may be avoided, and adverse influences of medicament 104b on the measured electric potential may be more reliably avoided. The flow of conductive gel layer 103 into adhesive layer 104 may also be avoided. That is, interference between conductive gel layer 103 and adhesive layer 104 may be avoided. Instead of adhesive layer 105, a stopper for avoiding interference between conductive gel layer 103 and adhesive layer 104 may be disposed in the position of adhesive layer 105. This stopper may have adhesive force or no adhesive force.

Figure 3:
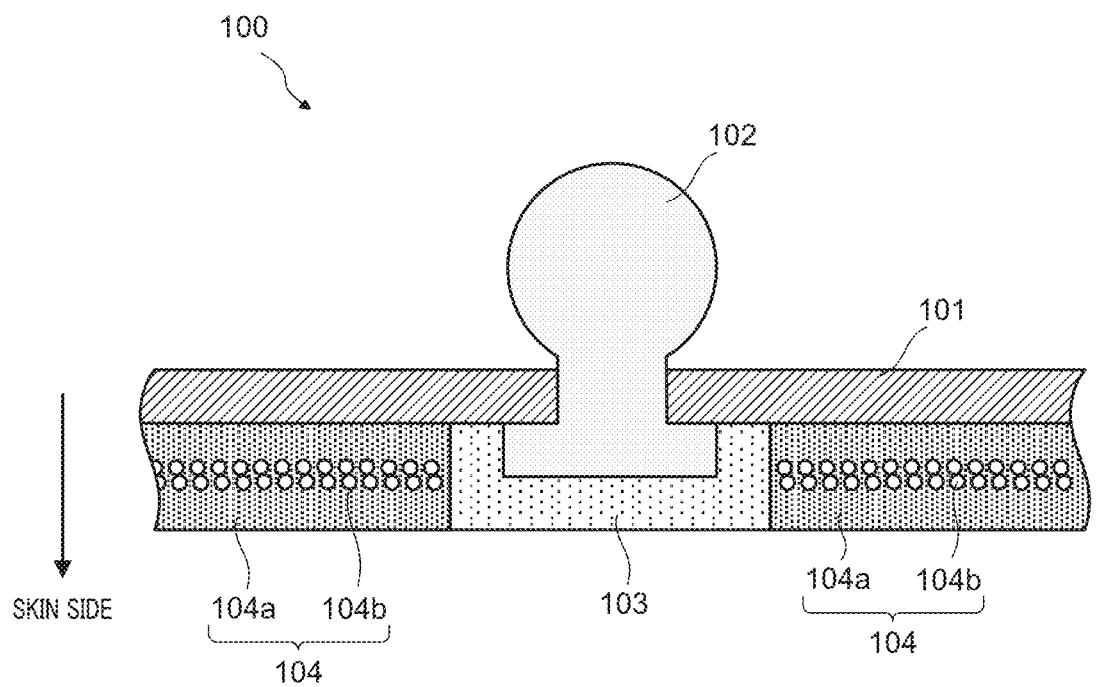
FIG. 3 is a cross sectional diagram illustrating another configuration example of the bioelectrode sheet.
Figure 4:
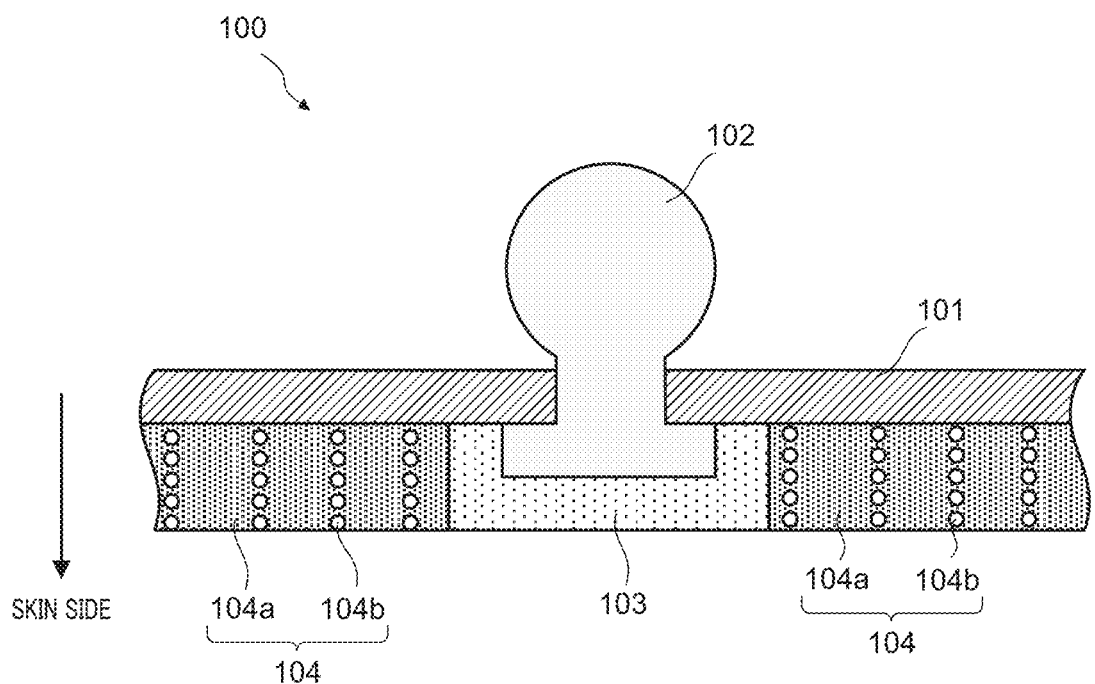
FIG. 4 is a cross sectional diagram illustrating another configuration example of the bioelectrode sheet.

The example of FIG. 1 illustrates a case where medicament 104b is uniformly mixed in adhesive layer 104. As illustrated in FIG. 3 and FIG. 4, for example, medicament 104b may be mixed in adhesive layer 104 in layers, and basically, the medicament may be partially mixed in the adhesive layer.

Since conductive gel layer 103 has also adhesive force, conductive gel layer 103 may be regarded as a sort of adhesive layer. However, according to the present embodiment, adhesive layer 104 is formed to be separated from conductive gel layer 103, and medicament 104b is mixed in adhesive layer 104. In practice, conductive gel layer 103 is preferably formed of a wet material to be sufficiently in close contact with the skin so as to have low contact resistance with the skin. On the other hand, adhesive layer 104 is formed of a material having higher adhesive force to the skin than conductive gel layer 103 and also having higher electric resistance than conductive gel layer 103 as described above.

A peeling sheet (not illustrated) is affixed to surfaces of conductive gel layer 103 and adhesive layer 104 on the skin side before bioelectrode sheet 100 is used, and a user peels off this peeling sheet from conductive gel layer 103 and adhesive layer 104 when bioelectrode sheet 100 is used and affixes conductive gel layer 103 and adhesive layer 104 to the skin of the subject.

Figure 5:
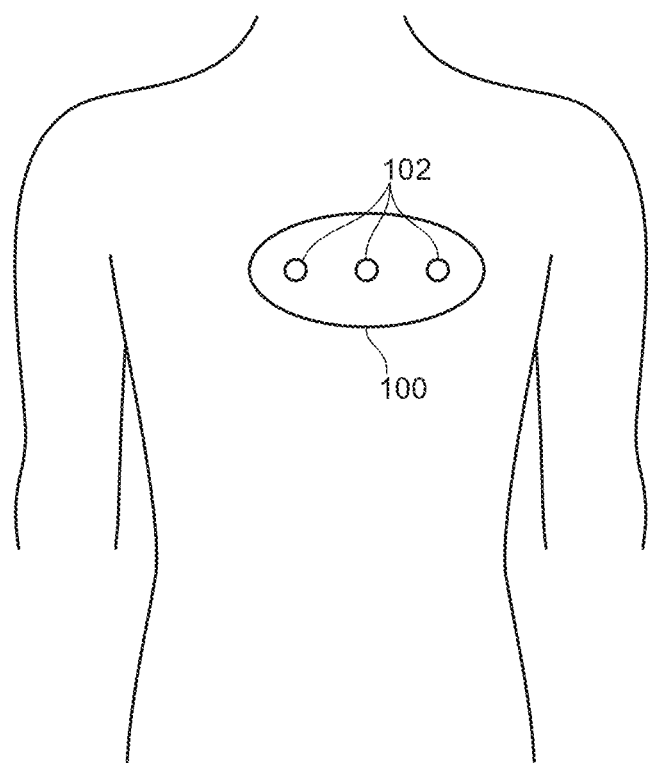
FIG. 5 illustrates a situation where the bioelectrode sheet is affixed to a subject.

FIG. 5 illustrates a situation where bioelectrode sheet 100 according to the present embodiment is affixed to the chest of the subject. Bioelectrode sheet 100 is affixed to the chest of the subject for a long period of time such as, for example, one to two weeks, and is used to obtain a Holter electrocardiogram or the like. With regard to bioelectrode sheet 100, plural electrodes 102 are disposed in one sheet. Among plural electrodes 102, for example, a middle electrode is an indifferent electrode, and electrodes on both sides are differential electrodes.

Figure 6:
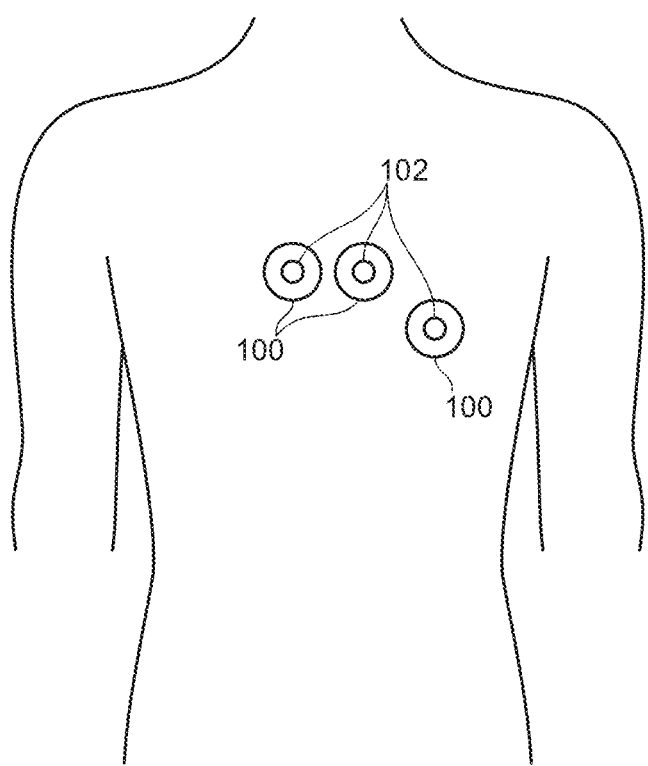
FIG. 6 illustrates a situation where the bioelectrode sheet is affixed to the subject.

A mode of bioelectrode sheet 100 is not limited to the mode in which plural electrodes 102 are disposed in one sheet to be integrated with the one sheet as illustrated in FIG. 5, and a mode may also be adopted in which one electrode 102 is disposed in one sheet, and respective bioelectrode sheets 100 are affixed to predetermined positions of the chest of the subject as illustrated in FIG. 6.

According to the present embodiment as described above, since medicament 104b is to be mixed in adhesive layer 104, medicament 104b may be distributed to a wide range substantially equivalent to the area of bioelectrode sheet 100 (excluding, of course, the part occupied by conductive gel layer 103). Thus, medicament 104b may be caused to permeate the skin from the wide range.

It should be noted that the configuration in which plural electrodes 102 are integrated with the one sheet as in the type illustrated in FIG. 5 is more beneficial since the permeation amount of medicament 104b to the skin may be increased while adhesive layer 104, that is, the area where medicament 104b is in contact with the skin may be enlarged.

In a case where plural bioelectrode sheets 100 are affixed as illustrated in FIG. 6, the type of the medicament or the amount of the medicament may also be changed for each bioelectrode sheet 100.

Herein, according to the present embodiment as described above, the medicament such as Bisoprolol working for the cardiovascular system is used as medicament 104b. With regard to the medicament for the cardiovascular system, medicinal benefits do not significantly change depending on affixed positions unlike poultice or the like. That is, affixed positions hardly make any difference. Thus, the present embodiment is suitable to a product where affixed positions are varied like the electrode for electrocardiogram measurement.

When the area of bioelectrode sheet 100 is large, the area of adhesive layer 104 is also large. Therefore, medicament 104b may be caused to permeate the living body from the wide range, and the permeation amount of medicament 104b may be increased.

As described above, according to the present embodiment, since medicament 104b is mixed in adhesive layer 104 disposed in the peripheral position of conductive gel layer 103 other than conductive gel layer 103 in the bioelectrode sheet to be affixed to the skin of the subject, it is possible to realize bioelectrode sheet 100 to be also usable for other purpose than the measurement of the biological information without decreasing measurement accuracy for biological information such as an electrocardiogram.

With regard to bioelectrode sheet 100 according to the present embodiment, since percutaneous absorption of medicament 104b and electrocardiogram measurement may be performed at the same time when one sheet is affixed, labor for affixing the medicament sheet may be alleviated as compared with a case where the bioelectrode sheet having no medicament 104b mixed therein and a medicament sheet such as cataplasm are separately affixed to the skin. In addition, inconvenience may occur that the medicament sheet hinders affixing of the bioelectrode sheet in a case where the medicament sheet is affixed earlier, but such inconvenience does not occur when bioelectrode sheet 100 according to the present embodiment is used.

Moreover, since bioelectrode sheet 100 according to the present embodiment may obtain the biological information while medicament 104b is caused to permeate the living body, change in efficacy by medicament 104b over time may be checked by the biological information. In a case where the electrocardiogram is to be measured by bioelectrode sheet 100 as in the embodiment, effects by medicament 104b for the cardiovascular system over time may be checked by the electrocardiogram. Thus, bioelectrode sheet 100 according to the present embodiment is suitable as the bioelectrode sheet for obtaining, for example, the Holter electrocardiogram that obtains the biological information for the long period of time.

In particular, bioelectrode sheet 100 is suitable for use at home. That is, the medicinal benefits may be checked when medicine is administered to a patient while a doctor or a nurse directly diagnoses the patient in a hospital. In a case where the patient takes the medicine by itself at home, since the doctor or the nurse does not directly diagnose the patient, it is difficult to directly check the medicinal benefits. Also at home, when the patient is in a state of wearing some kind of biological information obtaining apparatus such as a Holter monitor, the medicinal benefits may be checked on the basis of the biological information obtained by the biological information obtaining apparatus, but the patient is not necessarily wearing the biological information obtaining apparatus when the patient takes the medicine. In contrast, since administration of the medication and obtainment of the biological information are combined for bioelectrode sheet 100 according to the present embodiment, the biological information may be regularly obtained at the time of the administration of the medication, and the medicinal benefits may be reliably checked also with regard to the administration of the medication at home.

In addition, according to the present embodiment, a fear is taken into account that, when the medicament is mixed in conductive gel layer 103, property of conductive gel layer 103 may change by the medicament to affect the measurement accuracy for the electrocardiogram. Thus, medicament 104b is mixed in adhesive layer 104 instead of mixing of the medicament in conductive gel layer 103.

A configuration in which the medicament is mixed in the conductive gel layer has also been proposed up to now as disclosed in PTL 4, but according to the configuration, as seen from PTL 4, a configuration of conductive gel is limited. In contrast, according to the present embodiment, since the medicament is not mixed in the conductive gel, a degree of freedom for a choice of the conductive gel is increased.

Figure 7:
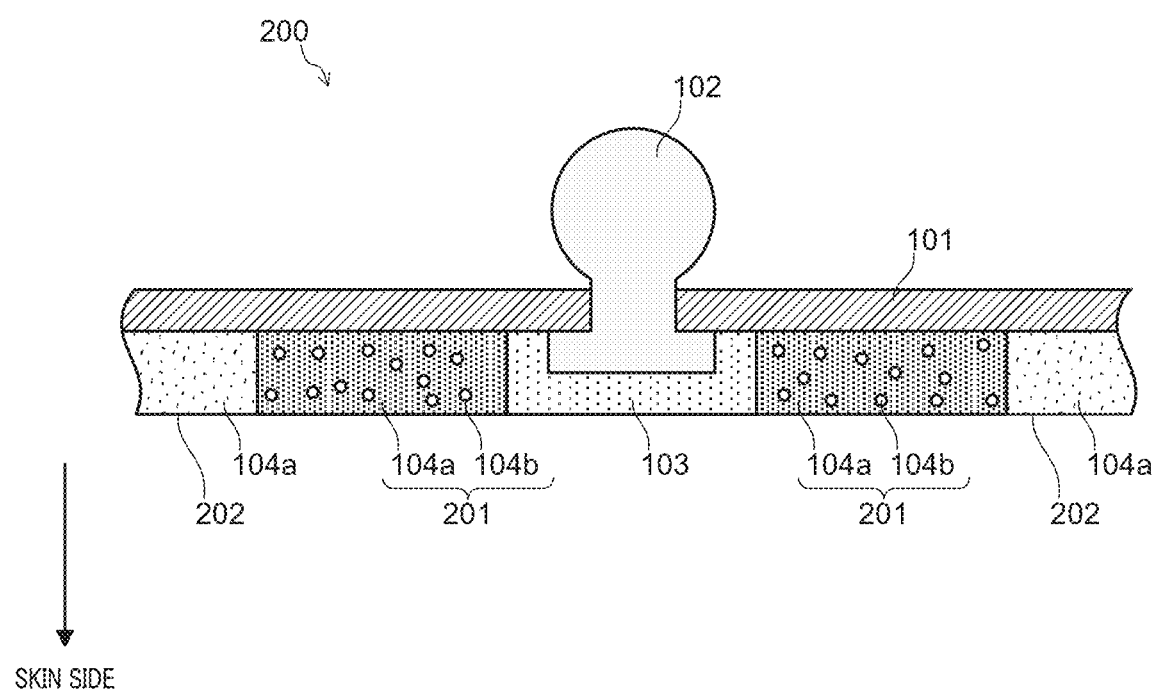
FIG. 7 is a cross sectional diagram illustrating another configuration example of the bioelectrode sheet.

According to the above-described embodiment, the case has been described where the part in contact with the skin is constituted by conductive gel layer 103 and adhesive layer 104, and medicament 104b is mixed in adhesive layer 104. As illustrated in FIG. 7, for example, a configuration may also be adopted in which the part in contact with the skin is constituted by conductive gel layer 103, first adhesive layer 201, and second adhesive layer 202, where medicament 104b is mixed in first adhesive layer 201, and the medicament is not mixed in second adhesive layer 202. With the above-described configuration, since the medicament does not need to be necessarily mixed in second adhesive layer 202, it is sufficient that the layer simply has only an adhesive function without taking the permeation of the medicament to the skin or the like into account. As a result, the adhesive force of second adhesive layer 202 may be easily set to be higher than the adhesive force of first adhesive layer 201. Therefore, when second adhesive layer 202 is disposed in the periphery of bioelectrode sheet 200, it may become more difficult for bioelectrode sheet 200 to be peeled off from the peripheral part. As illustrated in FIG. 2, adhesive layer 105 equivalent to a second adhesive layer may also be disposed between conductive gel layer 103 and adhesive layer 104.

The above-described embodiment merely illustrates specific examples for carrying out the present invention, and a technical scope of the present invention is not to be restrictively construed by these examples. That is, the present invention may be carried out by various forms in a range without departing from the gist or main features thereof.

According to the above-described embodiment, the case has been described where the bioelectrode sheet according to the present invention is used for electrocardiogram measurement, but the bioelectrode sheet according to the present invention may also be used to measure a bioelectric signal such as an electromyogram other than the electrocardiogram.

The disclosure of Japanese Patent Application No. 2017-051690, filed on Mar. 16, 2017, including the specification, drawings, and abstract, is incorporated herein by reference in its entirety.

INDUSTRIAL APPLICABILITY

The present invention is widely applicable to the bioelectrode sheet including the electrode for biological information measurement and being affixed to the skin of the subject.

REFERENCE SIGNS LIST

100, 200 Bioelectrode sheet
101 Base
102 Electrode
103 Conductive gel layer
104 Adhesive layer
104a Adhesive agent
104b Medicament
105 Adhesive layer (stopper)
201 First adhesive layer
202 Second adhesive layer

What is claimed is:

1. A bioelectrode sheet to be affixed to a skin of a subject, the bioelectrode sheet comprising:
    a sheet-like base including first and second surfaces;
    an electrode held by the base, at least a part of the electrode being disposed on a side of the first surface of the base;

a conductive gel layer that covers the at least part of the electrode disposed on the side of the first surface of the base and is exposed to the side of the first surface; and an adhesive layer that is disposed in a position different from the conductive gel layer of the base and is exposed to the side of the first surface in a position different from the conductive gel layer, wherein the adhesive layer includes medicament mixed in the adhesive layer, wherein:

the adhesive layer includes a first region where the medicament is mixed and a second region where the medicament is not mixed, the second region is disposed between the conductive gel layer and the first region and surrounds an outer periphery surface of the conductive gel layer, and the second region prevents the medicament from flowing into the conductive gel layer from the first region.

2. The bioelectrode sheet according to claim 1, wherein:
the electrode and the conductive gel layer are disposed in a central part of the base; and
the adhesive layer is disposed on a peripheral side of the base relative to the electrode and the conductive gel layer.

3. The bioelectrode sheet according to claim 1, wherein the second region has higher adhesive force than the first region.

4. The bioelectrode sheet according to claim 1, wherein the bioelectrode sheet is a bioelectrode sheet for electrocardiogram measurement to be affixed to a chest of the subject.

5. The bioelectrode sheet according to claim 1, wherein the medicament is medicament for a cardiovascular system.

* * * * *